Figure 1:
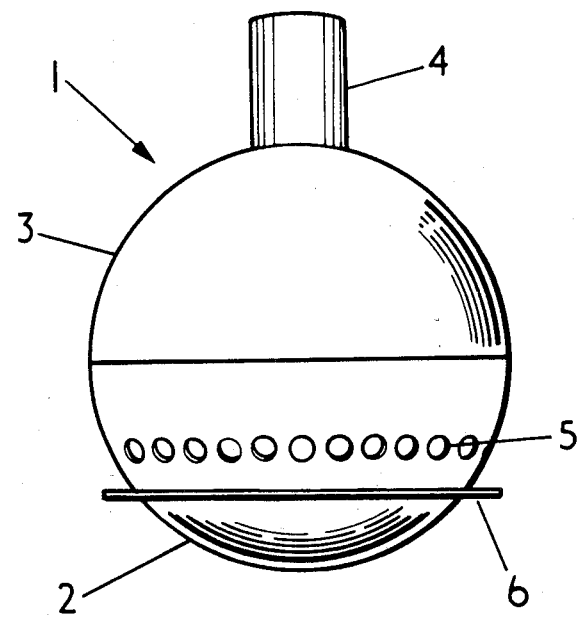

United States Patent [19]

Vincent et al.

[11] Patent Number: 4,586,389
[45] Date of Patent: May 6, 1986

[54] DUST DETECTION

[75] Inventors: James H. Vincent; David Mark, both of Haddington; Harold Gibson; Gordon Lynch, both of Edinburgh, all of Scotland

[73] Assignee: Coal Industry (Patents) Limited, London, England

[21] Appl. No.: 539,140

[22] Filed: Oct. 5, 1983

[30] Foreign Application Priority Data

Oct. 22, 1982 [GB] United Kingdom ................. 8230297

[51] Int. Cl.$^4$ ............................................... G01N 1/16
[52] U.S. Cl. .................................. 73/863.22; 55/270; 55/317; 55/403; 55/462; 55/524
[58] Field of Search ................ 55/270, 317, 462, 403, 55/524; 73/28, 38, 863, 863.03, 863.22, 864.31

[56] References Cited

U.S. PATENT DOCUMENTS

| | | | |
|---|---|---|---|
| 2,819,774 | 1/1958 | Schmidt et al. | 55/270 |
| 3,304,783 | 2/1967 | Quigley | 73/28 |
| 4,046,593 | 9/1977 | Au et al. | 55/270 |
| 4,274,846 | 6/1981 | Smith | 55/270 |
| 4,321,822 | 3/1982 | Marple et al. | 55/270 |

OTHER PUBLICATIONS

Ogden et al.–Inhalable Dust Sampler for Measuring the Hazard from Total Airborne Particulate (1978), Annal of Occupational Hygiene, vol. 21, pp. 41-50.
Lundrgren–Aerosol Sampler for Determination of Particle Concentration as a Function of Size & Time, Apr. (1967), vol. 17, No. 4 Journal of Air Pollutron Control Assn., vol. 17, No. 4, pp. 225-228.

Primary Examiner—Bernard Nozick
Attorney, Agent, or Firm—James C. Wray

[57] ABSTRACT

A portable aerosol dust spectrometer has an inlet section with a sampler entry having an entry efficiency for airborne dust approximately to that of the human head during inhalation, a clean-up stage to remove particles above 15 μm and a main collection stage which is a cascade impactor. The cascade impactor classifies particles of dust and collects fractions onto a number of collection surfaces. A pump draws air or gas through the apparatus. The apparatus samples air in a similar way to the human body and yields fractions of dust for further study.

9 Claims, 3 Drawing Figures

DUST DETECTION

This invention concerns improvements in dust detection and more especially concerns an inhalable dust aerosol spectrometer.

The sampling of dust in air is an important aid to improving the working and living environment. There have been developed a number of devices over the years which sample and collect dust in air. An early successful example was the "MRE Gravimetric Dust Sampler" designed by the National Coal Board and marketed by Casella which selects dust aerodynamically by elutriation, so that fine particles thought to be reasonably representative of the ones deposited in the alveolated region of the lung can be collected on a filter and weighed. This device has been widely used in the British coal mining industry and enabled establishment of the relationship between cumulative mass concentration of respirable dust in mine air and the risks of developing pneumoconiosis among the workforce. Other particle selecting devices have been designed and used for essentially similar purposes in mining and other industries and have achieved similar results, so that it can be concluded that in many dust-related diseases of the lung, it is the respirable component which is primarily responsible. However, there exist particles of airborne dust which, after inhalation, do not necessarily reach the alveolar regions of the lung but are deposited elsewhere in the respiratory tract, for example in the nasopharyngeal (the head down to and including the larynx) or the tracheobronchial (the trachea and the bronchial tree down to the terminal bronchioles) regions, and which are sufficiently toxic or irritating to cause illness. It is therefore an aim of the present invention to provide a portable instrument which first samples air in a similar way to the human body during inhalation and then permits the fractionation of the dust thus sampled to give desired deposition fractions for further study, the instrument yielding biologically-relevant dust fractions.

The present invention provides a portable aerosol dust spectrometer having an inlet section comprising an inhalable dust sampler entry having an entry efficiency for airborne dust approximating to that of the human head during inhalation, a clean-up collection stage which is effective in removing substantially all particles above 15 $\mu$m (which are not capable of penetrating beyond the larynx) and a main collection section comprising a cascade impactor capable of aerodynamically classifying particles of less than 15 $\mu$m and collecting fractions therefrom on a plurality of collection surfaces without substantial losses of particles due to gravity or impact with surfaces of the impactor which are not intended to constitute collection surfaces, and pump means for drawing air or other gas through said inlet and collection sections.

An essential feature of the present invention is the inhalable dust sampler entry. It is not widely realised that a preliminary aerodynamic selection of dust particles in air is made by the human body in the act of breathing, and that this is largely dependent upon the aerodynamic size of the particles. For example, dust sampling is currently done on a basis in which there is no attempt to differentiate between dust particles which would not be inhaled and those which are. The importance of this may be illustrated by the fact that considering particles of 30 $\mu$m diameter, only about 40 to 60% of those detected on a "total dust" basis are inhaled through the nose and mouth. Even at very small aerodynamic diameters such as 5 $\mu$m, the inhalation efficiency is in a range of about 85 to 97%. To achieve good operation of the inhalable dust sampler, it appears necessary that the volumetric flow rate should be reasonably high, preferably at least 2 liters per minute, and hence the pump means should be matched to achieve the desired sampling efficiency curve over the 0–15 $\mu$m particle size range when using the inhalable dust sampler. A preferred inhalable dust sampler is a development of the ORB entry described by Ogden and Birkett in "Annals of Occupational Hygiene" Vol. 21, 1978, pp. 41–50. It is essentially spherical in shape with a plurality of entry holes at the same latitude, preferably at about 20° latitude. Preferably, the sphere has a flat annular strip or "halo" mounted at a higher latitude than the entry holes, suitable at about 33° latitude. The configuration of the preferred inhalable dust sampler may be more readily appreciated by reference to the accompanying drawings and the associated description hereinafter.

The cascade impactor is preferably a development of an instrument described by Lundgren in "Journal of the Air Pollution Control Association" Vol 17 No 4, April 1967, p 225. The Lundgren impactor uses coated circular, drum-type collection surfaces, with the particularly useful attribute that rotation of the drum at a steady speed can provide a chronological record of dust collected on the surface. The Lundgren impactor utilises four cascade impactor stages, each consisting of a nozzle providing an elongate slit with a collection drum mounted close to the slit so that air leaving the slit impinges upon the collecting drum. Coarse airborne particles tend to deposit on the drum while fine ones tend to pass around the outside. By decreasing the width of the slit and moving the drum closer, smaller particles impinge upon the collection surface. We have found, however, that despite its advantages, the Lundgren impactor as shown in the paper suffers from serious losses which distort the value of the information obtainable therefrom. We believe that the formation of eddies, gravitational settling and inertial impaction of particles with the internal surfaces which are not collection surfaces (wall losses) cause losses which are substantial, for example of the order of 30% for particles of about 8 $\mu$m diameter. Wall losses can be significantly reduced by careful internal design, for example in the present invention the preferred method is to use rotating drum collection surfaces positioned within a shaped block so that an annular space is provided around each drum and the intake flow rate and the dimensions of the annular space are chosen to achieve an air speed in the annular space which is sufficiently high to prevent gravitational deposition of particles but not so high as to cause substantial further impaction and wall losses.

Preferably, the collection surface of each collection drum, including that of the clean up collection stage, is coated with a sticky substance to regain dust particles. There are many suitable viscous coatings, although a grease such as vacuum grease is preferred. To assist in handling the collected dust samplers, it is preferred for each collection drum to removably carry a plastics membrane which is suitably greased; the membrane may then be dismounted for study. The drums, as has been suggested, are preferably continously and synchronously driven, and this may be achieved by high quality spring-driven clockwork mechanisms with the appropriate gearing, or by electric motors. Alterations to the gearing may be made to permit different sampling times.

The pump means is suitably chosen for the duty necessary, as is conventional, although if the instrument is intended for hazardous invironments, it will be necessary to take into account requirements for flameproofing the power source and/or other safety measures. As has been indicated, a relatively high volumetric flow rate is desirable to provide for efficient operation of the inhalable dust sampler and to provide sufficiently high gas velocities for the impactor to operate, and to provide sufficient dust deposits to allow their gravimetric assessment. The actual flow rate will depend upon the chosen dimensions of the instrument as a whole.

It has been found that the cascade impactor described is not capable of collecting particles of less than about 1 $\mu$m, and if these form a significant part of the particle size distribution of the dust, from a mass or toxicity point of view, then it is preferred to incorporate a final collection stage such as a fine filter capable of collecting particles below 1 $\mu$m in size. It has to be borne in mind that such a filter exhibits a substantial pressure drop across it and therefore a more powerful pump means has to be used to maintain the desired flow rate.

Figure 2:
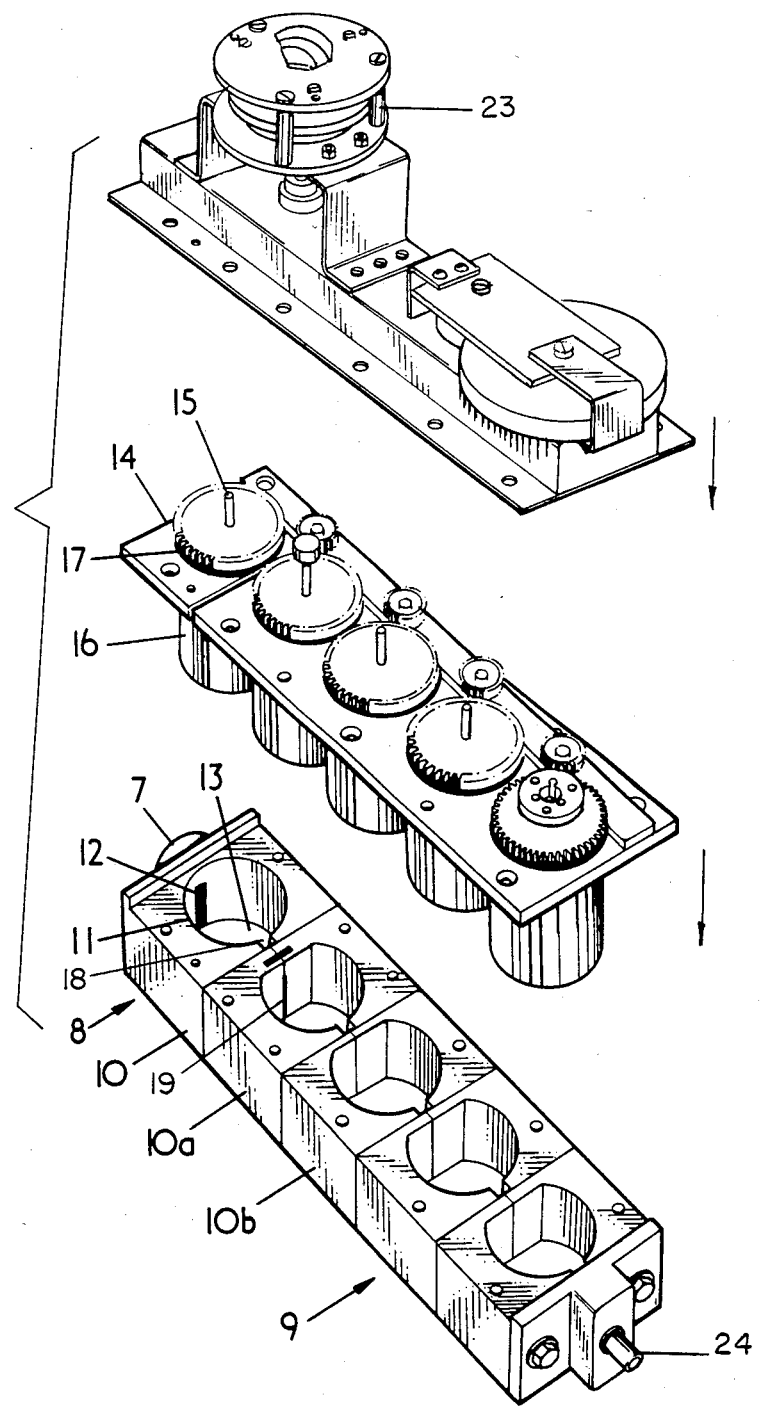
Figure 3:
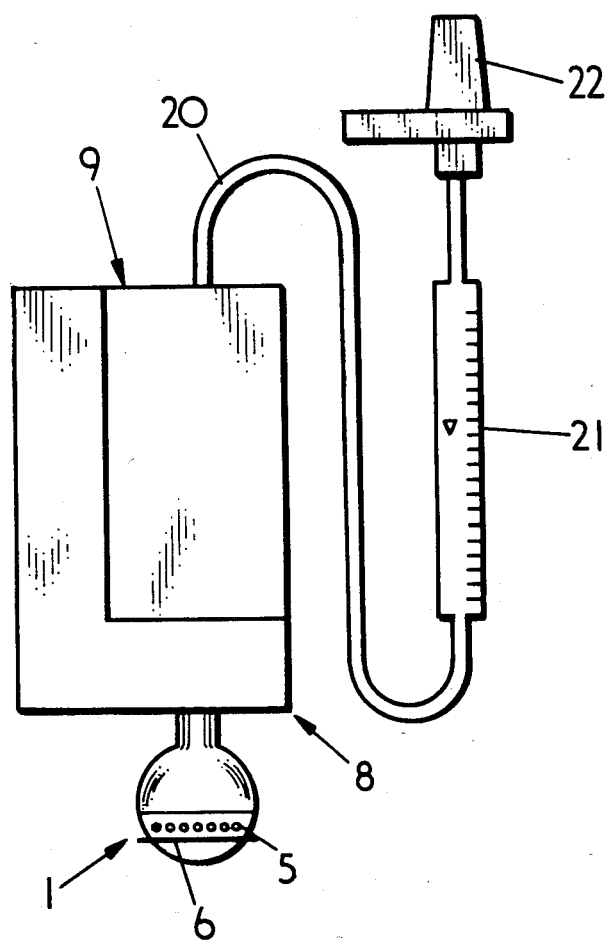

The invention will now be described with reference to the accompanying drawings, in which FIG. 1 is a side view of an inhalable dust sampler entry, FIG. 2 is an exploded perspective view of a cascade impactor incorporating a clean up collection stage and four main collection stages, and FIG. 3 is a schematic diagram of an assembled sampler according to the invention.

Referring to FIG. 1, an inhalable dust sampler entry, 1, to be incorporated into a portable aerosol dust sampler according to the invention, is shown. The sampler entry has a first hollow hemispherical section, 2, and a second hollow hemispherical section, 3, which has an outlet connection pipe, 4. The hemispherical sections are metal pressings. The first section carries 32 spaced apart entry holes, 5, centred on a 20° latitude and mounted at a 33° latitude is an annular rim or halo, 6. The halo has been found to improve the sampling characteristics of the entry in relation to inhalable dust. The connection pipe is fitted into an inlet connection, 7, in the combined clean-up collection stage and cascade impactor shown in FIG. 2.

Referring now to FIG. 2, a clean-up collection stage generally indicated by 8, is attached to a cascade impactor generally indicated by 9. The collection stage consists of a metal block, 10, machined to form a circular cavity, 11 and having a slot, 12 connecting with the inlet 7. The block 10 is closed on one end by a metal base plate, 13, common to the collection stage and impactor and has a top plate, 14 through which is mounted a spindle, 15 carrying a collection cylinder, 16, and a toothed drive wheel, 17. The cavity has an exit slot 18 connecting with the first stage entry slot 19 of the cascade impactor. The cascade impactor is constructed analogously, having four stages; each stage having a separate block 10a, 10b etc bolted together with the block 10 of the clean-up collection stage. This was done for ease of manufacture in the prototype and although it is possible to conceive of a single block for clean-up stage and impactor no leaks were detected when the blocks were bolted together, without the need for gaskets. It will be observed that the shape of the cavities is different for the impactor stages in having a flattened edge which carries the entry slot for each stage. The slots are progressively narrowed, and the collection cylinders are progressively positioned closer to the slots, in order to collect progressively smaller particles. The size of the slots, the position of the cylinder and the air velocity are chosen to provide nominal cut sizes ($50^d$ae) of 12 $\mu$m (stage 1), 6 $\mu$m (stage 2), 3 $\mu$m (stage 3) and 1 $\mu$m (stage 4). I would be desirable in principle to have a larger number of stages in the impactor, but at least in the prototype instrument factors such as the size and weight of the whole instrument to provide ease of portability for carriage in underground coal mines effectively limited the number to four. Each cylinder is driven synchronously by a gear arrangement by means of a clockwork motor, 23. If a significant portion of the dust being sampled is less than one $\mu$m then it is preferred to incorporate a final collection stage, such as a fine filter capable of collecting particles below one $\mu$m in size. This filter 23 is located between the cascade impactor 9 and pump 22.

An outlet, 24, from the impactor is connected by a wide bore plastics tube, 20, suitably via a flow rate measuring device such as a "Rotameter", 21, to a pump, 22. A suitable flow rate of 10 liters per minute for the prototype instrument was achieved using the intrinsically-safe centrifugal fan and battery power pack from the "TBF50" dust sampler marketed by Mollider & Muller, Cologne, West Germany.

For use, each cylinder, including that of the clean-up stage, has a thin polycarbonate film carrying a uniform coating of a silicone grease, applied thereto, also using the grease as an adhesive to removably bond the film onto the cylinder. After a sampling period, for example on 8-hour shift sampling period, the instrument having been mounted in a suitable position, preferably at about average head height, the films are removed for examination.

A number of different methods can be used for analysing the results obtained in the form of dust deposits on the film. Included in these are optical microscopy (bands of different coloured dust deposits can easily be seen, corresponding to periods of rock cutting as contrasted with coal cutting in underground mines), direct weighing to obtain the masses collected (although this does not readily give information about the masses collected during shorter time periods within the longer overall sampling period) and, preferably, radiation reflectance or attenuation systems. Most preferably, the films carrying the dust deposits are analysed by attenuation of low-energy $\beta$-particles. The technique is known, and suitably uses a radiation source such as $^{14}$C and a $\beta$-particle detector, for example one marketed by Nuclear Enterprises Limited and using an anthracene crystal scintillator. The films can be scanned using a suitable mechanical arrangement, and valuable information on the deposits of dust obtained over the sampling period is obtained. An important asset of such a system is that the $\beta$-particle attenuation record is easily retained, enabling subsequent analysis at a much later date, and at the same time the classification of the dust onto the various sampling films by means of aerodynamic diameter is believed to give all the necessary data for epidemiological research.

A prototype version of the instrument according to the present invention was successfully tested in the laboratory and later in two underground coal mines having rather different environments.

We claim:

1. A portable aerosol dust sampler having an inlet stage, comprising:

inhalable dust sampler entry means having an entry efficiency for airborne dust approximately that of the human head during inhalation, cascade impactor means connected to an outlet of the inhalable dust sampler entry means having a block with a series of substantially cylindrical chambers each having entry and exit means, wherein a first chamber is cylindrical and subsequent chambers have flattened entry walls, wherein each exit means is aligned with each entry means of each succeeding chamber, and wherein the inlet means of each chamber is progressively smaller in a downstream direction, each chamber having mounted therein a rotatable cylinder, wherein the cylinders are positioned progressively closer to the entry means in a downstream direction, said cylinders having associated drive means, and pump means connected to an outlet of the cascade impactor means for drawing air or other gas through said entry means.

2. A dust sampler as claimed in claim 1, wherein a collection surface on each cylinder comprises a removable plastic membrane coated with a sticky substance to retain dust particles.

3. A dust sampler as claimed in claim 2, further comprising a final filter stage disposed between the cascade impactor and the pump means for collecting particles below 1 m in size.

4. A dust sampler as claimed in claim 3, wherein the dust sampler entry means comprises a substantially spherical hollow body having at least one entry hole.

5. A dust sampler as claimed in claim 4, wherein the hollow body of the dust sampler entry has a plurality of entry holes at the same latitude.

6. A dust sampler as claimed in claim 5, wherein the hollow body has a flat annular strip mounted externally at a higher latitude than the entry holes.

7. A cascade impactor apparatus for use with an inhalable dust sampler and pump means for draining air from the inhalable dust sampler through the cascade impactor, comprising, an inlet connected to the inhalable dust sampler, an outlet connected to the pump means, a series of blocks disposed between the inlet and the outlet, each block having a transverse circular cavity extending therethrough, and an entry slot and an exit slot axially aligned with the inlet and outlet, wherein a portion of the circular cavity is flattened at the entry slot of all but the first block, the first block being disposed adjacent the inlet, a base plate mounted on one side of the blocks and providing a mutual closure for the transverse circular cavity for each block, a top plate mounted on the opposite side of the blocks, the top plate supporting a rotatable cylinder within each circular cavity, means for rotating in synchronization the rotatable cylinders, each entry slot becoming progressively narrowed from the inlet to the outlet, wherein each block collects fractions of progressively smaller particles, and wherein each cylinder is mounted progressively closer to the entry slots in a downstream direction.

8. The apparatus of claim 7 wherein each rotatable cylinder has a thin polycarbonate film carrying a uniform coating of silicon grease.

9. The apparatus of claim 7 wherein each rotatable cylinder carries a removable membrane having a grease coating.

* * * * *